United States Patent [19]
Hergenrother et al.

[11] Patent Number: 5,852,189
[45] Date of Patent: Dec. 22, 1998

[54] TERTIARYAMINOALKYLLITHIUM INITIATORS AND THE PREPARATION THEREOF

[75] Inventors: William L. Hergenrother, Akron; Michael L. Kerns, Elyria; David F. Lawson, Uniontown, all of Ohio

[73] Assignee: Bridgestone Corporation, Tokyo, Japan

[21] Appl. No.: 777,646

[22] Filed: Dec. 31, 1996

[51] Int. Cl.$^6$ .............................. C07D 223/06; C08F 4/48
[52] U.S. Cl. ..................... 540/582; 540/450; 540/476; 540/477; 540/484; 546/345; 546/346; 546/348; 548/400; 564/463; 564/510; 502/157; 526/180; 526/340
[58] Field of Search ................. 260/665 R; 540/484, 540/612, 582, 450, 476, 477; 546/345, 346, 348; 548/560, 564, 400, 579; 564/463, 510; 526/180, 335, 337, 340; 502/157

[56] References Cited

U.S. PATENT DOCUMENTS

| | | |
|---|---|---|
| 5,491,230 | 2/1996 | Lawson et al. . |
| 5,493,038 | 2/1996 | Hall et al. . |
| 5,496,940 | 3/1996 | Lawson et al. . |
| 5,523,364 | 6/1996 | Engel et al. . |
| 5,527,753 | 6/1996 | Engel et al. . |
| 5,550,203 | 8/1996 | Engel et al. . |
| 5,610,237 | 3/1997 | Lawson et al. ..................... 526/180 X |

FOREIGN PATENT DOCUMENTS

| | | |
|---|---|---|
| 0 316 255 | 5/1989 | European Pat. Off. . |
| 0 316 255 A2 | 5/1989 | European Pat. Off. . |

OTHER PUBLICATIONS

An article entitled "3–Dimethylaminopropyl–Lithium–An Analytical and Kinetic Investigation of a New Initiator system for Polymer Synthesis," by C. D. Eisenbach, H. Schnecko, and W. Kern, *European Polymer Journal*, vol. 11, pp. 699–704, Pergamon Press, 1975.

An article entitled "Anionic Functional Initiators. 1: 3–Dimethylaminopropyllithium as an Initiator for the Synthesis of Bi–and Difunctional Polybutadienes," by Malcolm J. Stewart, Neil Shepherd and David M. Service, *British Polymer Journal* 22, (1990), pp. 319–325.

An article entitled "Anionic Polymerization of Isoprene, Butadiene and Styrene with 3–Dimethylaminopropyllithium," by Stergios Pispas, Marinos Pitsikalis and Nikos Hadjichristidis, Department of Chemistry, University of Athens, Greece, and Patrizia Dardani and Francesco Morandi, Milano, Italy, *Butterworth Heinemann Polymer*, vol. 36, No. 15, pp. 3005–3011, 1995.

An article entitled "Preparation of Polystyrene Labeled with Amino Groups at Specific Sites" by D. J. Worsfold, *Journal of Polymer Science:* Polymer Chemistry Edition, Vo. 21, pp. 2237–2240 (1983). Published by John Wiley & Sons, Inc.

*Primary Examiner*—Fred Teskin
*Attorney, Agent, or Firm*—Daniel N. Hall

[57] ABSTRACT

Relatively pure tertiaryaminoalkyllithium initiators suitable for anionic polymerization reactions are prepared at low temperatures in an organic ether by reacting an equivalent excess of lithium metal with a tertiaryaminoalkylhalide. The lithium initiators are very stable at moderate temperatures when the ether is replaced by an aliphatic, a cycloaliphatic, or an aromatic solvent. Yields of the initiator in excess of 98% are readily achieved.

15 Claims, No Drawings

TERTIARYAMINOALKYLLITHIUM INITIATORS AND THE PREPARATION THEREOF

FIELD OF THE INVENTION

The present invention relates to ambient temperature stable tertiaryaminoalkyllithium initiators and to a process for forming the same. More specifically, the present invention relates to the efficient preparation of relatively pure tertiaryaminoalkyllithium initiators.

BACKGROUND OF THE INVENTION

Heretofore, tertiaryaminoalkyllithium initiators were synthesized in tetrahydrofuran at low temperatures such as below minus 20° C. A disadvantage of such initiators was that they were unstable at temperatures above minus 20° C. and that compositions thereof generally contain low yields such as less than 50%. Such initiators could also be synthesized in hydrocarbon solvents but only at high temperatures such as at least 80° C. which gave rise to undesirable Wurtz Coupling Products.

SUMMARY OF THE INVENTION

Tertiaryaminoalkyllithium initiators for use in anionic polymerizations, e.g., rubber forming monomers, are prepared in organic ethers such as dimethylether at or below temperatures of the boiling point of the ether. The reaction is very efficient inasmuch as high yields, for example, at least 95, 98 and about 100 percent are obtained by using a ratio of at least two moles of the lithium metal per mole of tertiaryaminoalkylhalide. The initiators a rendered stable at ambient temperatures by replacing the ether with an aliphatic, cycloaliphataic or hydrocarbon solvent having from about 5 or 6 to about 30 carbon atoms. The lithium atom can be directly attached to the nitrogen through a single or multiple carbon atom linkage or via a tethering carbon atom chain in a ring or cycloaliphatic compound. The initiators of the present invention are suitable for the anionic polymerization of rubber forming monomers containing from 4 to 10 carbon atoms such butadiene, isoprene, or monomers of butadiene and styrene.

DETAILED DESCRIPTION OF THE INVENTION

The tertiaryaminoalkyllithium initiator compositions of the present invention are derived from the reaction of tertiaryaminoalkylhalides with an excess of a lithium metal which results in the lithium replacing the halide. The halide preferably is a chloride. The starting halide compound has an intermediate alkyl or cycloalkyl group with one end or terminal portion having a halide thereon and the other end or terminal portion containing a tertiaryamine. Examples of specific formulas of such tertiaryaminoalkylhalides include $$R^1-\underset{\underset{R^2}{|}}{N}-R-X \qquad \text{Formula I}$$

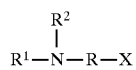

Formula II

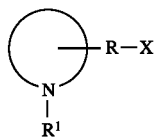

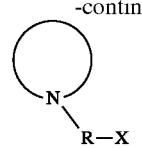

Formula III

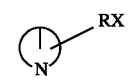

Formula IV

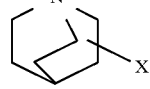

Formula V where X is a halide, preferably chloride, and R is an alklylene or a cycloalkylene having from 1 to 10 carbon atoms with from 1 to 3 carbon atoms, e.g., methylene, or propylene, being preferred. The $R^1$, $R^2$ groups, independently, can be an alkyl having from 1 to 12 carbon atoms, and preferably from 1 to 4 carbon atoms. Often times, the two alkyl groups of the nitrogen atom are joined or connected together so as to form a ring or cycloalkyl structure with the total number of carbon atoms therein being from 2 to 12 carbon atoms with from 4 to 6 carbon atoms being preferred. When a ring structure exists as in Formulas II through V, the intermediate alkyl or cycloalkyl group R can be directly connected to the nitrogen atom as in Formula III or to any carbon atom of the ring as in Formula II. Moreover, the one or more rings can have one or more alkyl substituents thereon, such as from one to four and preferably one or two substituents with the alkyl substituent containing from one to four carbon atoms with one or two carbon atoms, that is, methyl or ethyl being preferred. Examples of suitable tertiaryaminoalkylhalides include 3-hexamethyleneiminepropyl chloride, or 2-(2-chloroethyl)-1-methylpyrolidine, or 3-chloromethyl-1-methylpiperidine or 3-dimethylaminopropyl chloride, or 3-pyrrolidinopropyl chloride, and mixtures thereof.

The excess of lithium metal is such that the mole ratio of lithium to tertiaryaminoalkylhalide is from about 2 to about 12, desirably from about 2 to about 9, and preferably from about 2 to about 4.

In order to obtain a high purity anionic initiator composition, it is an important aspect of the present invention to utilize an organic ether, for example $R^3$-O-$R^4$ wherein $R^3$ and $R^4$ independently, is an alkyl having from 1 to 4 carbon atoms with methyl being preferred. Since organic ethers containing a high carbon atom alkyl group generally do not give good yields, preferably at least one of the alkyl groups is methyl and desirably the other alkyl group is methyl or ethyl. Examples of organic ethers include methyl t-butylether, methylpropylether and methylethylether with dimethylether being preferred. The reaction temperature of the lithium with the tertiaryaminoalkylhalide in the presence of the ether is at or below the boiling point of the ether and for dimethyl ether it is at least minus 24° C. (i.e. −24° C.) and desirably from about minus 25° C. to about minus 78° C. The reaction is generally carried out at or slightly above atmospheric pressure, e.g., from about 1 to about 4 or 6, and preferably from about 1.1 to about 2 atmospheres to help maintain an inert atmosphere. The time of the reaction generally varies with the type of tertiaryaminoalkylhalide utilized and the time required for the reaction to run to completion, e.g. to at least 95% or 98% conversion of all tertiaryaminoalkylhalides to a tertiaryaminoalkyllithium.

The process of the present invention results in very high yields (i.e. percent conversion of all tertiaryaminoalkylhalides to tertiaryaminoalkyllithiums) such as at least 60, 70, or 80 percent, desirably at least 90 or 95 percent, and preferably at least 98 or 99 percent and even about 100 percent.

The solvents in which the anionic initiator compositions of the present invention are soluble desirably include alkanes, or cycloalkanes, or aromatics including alkyl substituted aromatics having a total of from about 5 or 6 to about 30 carbon atoms and which are generally liquid at a moderate temperature. By the term "moderate temperature," it is meant that the tertiaryaminoalkyllithium initiators are stable at temperatures of from about minus 20° C. to about 60° C., desirably from about 0° to about 45° C. and preferably from about 10° to about 30° C. Examples of suitable solvents include pentane, hexane, cyclohexane, heptane, octane, decane and dodecane. Hexane, cyclohexane, and substituted alkyl cyclohexane such as methylcyclohexane are preferred. Also included within such solvents are high molecular weight hydrocarbons such as conventional mineral oils.

Stable tertiaryaminoalkyllithium compositions are formed by adding the solvent to the reaction mixture which contains the organic ether and removal of the ether. The solvent can be added either before, during, or after removal of the ether. A preferred route is to generally add a solvent such as cyclohexane slowly over a time interval of perhaps 20 minutes to an hour and at the same time slowly vaporizing the ether by raising the temperature of the reaction vessel and/or applying a vacuum. The amount of the solvent is 60 to 99 percent by weight based upon the total weight of the anionic initiator composition and solvent when the ether has been removed. The concentration of the tertiary aminoalkyllithium is thus often from about 0.1 to about 1.5 moles per liter.

The process of preparing the tertiaryaminoalkyllithium initiators of the present invention results in high purity initiator compositions having only small or trace amounts of other components therein such as ether, by-products (e.g., LiCl), or polar modifiers. That is, the amount of the anionic initiator is at least 60, 70, 80, or 90 percent, desirably at least 95 or 97 percent, or often at least 98 or 99 percent by weight based upon the total weight of the initiator and the reaction solution such as the by-products, the polar modifiers, etc., but excluding the solvent carrier, the LiCl, and the ether. It also avoids the disadvantages of the tetrahydrofuran route in which the initiator is unstable at temperatures above minus 20° C. or the hydrocarbon route in which undesirable Wurtz coupling products are formed. The purity of the compositions of either of the above prior art routes is generally less than 50 percent by weight. Moreover, good initiator stability in the hydrocarbon solvent is obtained for periods of weeks and even months. That is, less than 1 mole percent, desirably less than 0.5 mole percent, and preferably less than 0.3 mole percent of the anionic initiator's decay at 20° C. during a period of one week.

The anionic initiators of the present invention are suitable for use in any anionic polymerization especially rubbers. Monomers which can thus be polymerized include conjugated dienes having a total of from 4 to 10 carbon atoms such as 1,3-butadiene, isoprene, 1,3-pentadiene, 2,3-dimethyl-1-3-butadiene, 2-methyl-1,3-pentadiene, 2,3-dimethyl-1,3-pentadiene, 2-phenyl-1,3-butadiene, and 4,5-diethyl-1,3-octadiene. Moreover, conjugated dienes can be polymerized in the presence of various vinyl-substituted aromatic monomers having a total of from 8 to 12 carbon atoms such as styrene, 1-vinylnaphthalene, 3-methylstyrene (p-methylstyrene), 3-5-diethylstyrene, and the like. The number average molecular weight of the polymers generated show good correlation with the calculated molecular weight.

Conventional modifiers can be utilized in association with the polymerization reaction to control various aspects such as the amount of 1,2, or 3, 4-vinyl repeat units or 1,4 repeat units of the formed rubber, e.g. through the utilization of OOPS (2,2'-ditetrahydrofuryl)propane), tetramethylethyldiamine, tetrahydrofuran, and the like. Moreover, the molecular weight ratio, i.e. Mn/Mw, have typical values of from about 1.05 to about 1.25.

A particular utility of the anionic initiators of the present inventions is in the polymerization of rubbers for tires such as tread rubber, carcass rubber, sidewall rubber, and the like.

The invention will be better understood by reference to the following examples which serve to illustrate but not to limit the invention.

EXAMPLE 1

Preparation of Dimethylaminopropyllithium

A 4-neck round-bottom flask was equipped with a dry-ice condenser, two vacuum adapters with stopcocks, a stir bar and a septum. The system was flame dried as it was subjected to 3 evacuate/fill cycles with argon. The system was then sealed off and placed in a glove box where lithium powder (0.099 mol, 0.688 g) was added to the flask. The flask was then re-sealed, removed from the glove box, and reconnected to the argon line via one of the vacuum adapters. To the other vacuum adapter was connected a cylinder of dimethyl ether. Dry-ice was added to the condenser and the flask was cooled in a dry-ice/acetone bath. Dimethyl ether (50 mL) was then condensed in the reaction flask with a regulated pressure of 5–10 psi. Excess gasses were vented via a by-pass mineral oil bubbler. After the desired amount of dimethyl ether had been collected (~65 mL), compound A, i.e., 3-dimethylaminopropylchloride (0.017 mol, 2.1 g) was added dropwise over 10 minutes to the rapidly stirred dispersion. The solution was stirred rapidly at (−78° C.) for 1.5 h then warmed to reflux (−24.8° C.) and held there for another 1.5 h. To the dispersion was then added dry, deoxygenated cyclohexane incrementally over 30 min while the dry-ice in the condenser was allowed to sublime away permitting the dimethyl ether to escape via the by-pass bubbler. The aminoalkyllithium solution was then filtered through a fritted glass tube under argon and stored in a Schlenk tube. Two aliquots (2 mL) of the sample were removed and quenched with $H_2O$ and TMSCl (trimethylsilylchloride) respectively. Analysis of the derivatized samples by GC/MS revealed no products arising via Wurtz coupling, nor any other significant side products. The aminoalkyllithium sample was titrated using a modified Gilman titration as a 0.24M solution. The active solution was used to polymerize butadiene affording head end-functionalized butadiene rubber polymers.

EXAMPLES 2–7

In a similar manner, other initiators were synthesized. Table I summarizes relevant data of initiators made from aminoalkylchlorides A through E as set forth below. The yield is not set forth in the first five examples, inasmuch as the solution was saturated, and accordingly, an accurate yield figure was not obtained.

AMINOALKYLCHLORIDES

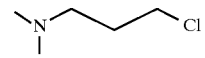

A

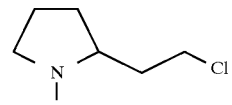

B

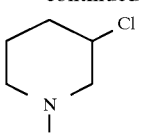

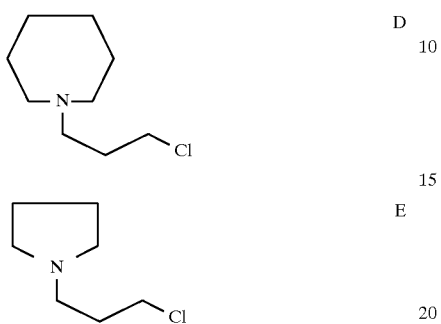

where A is 3-dimethylaminopropyl chloride;

where B is 2-(2-chloroethyl)-1-methylpyrrolidine;

where C is 3-chloromethyl-1-methylpiperidine;

where D is 3-hexamethyleneiminepropyl chloride, and where E is 3-pyrrolidinopropyl chloride.

TABLE I

| Example | Amino-alkyl-chloride | mmols Chloride | mmols Li | mL Di-methylether | Cyclo-Hexane | Time @ -78° C. | Time @ -24.8° C. | Molar Conc. RLi | Purity | Yield |
|---|---|---|---|---|---|---|---|---|---|---|
| 1 | A | 17 | 99 | 65 | 50 mL | 90 min. | 90 min. | 0.24 | 91% | — |
| 2 | B | 14.3 | 89.4 | 65 | 50 mL | 30 min. | 90 min. | 0.22 | 97% | — |
| 3 | B | 13.6 | 81.5 | 60 | 50 mL | 180 min. | 90 min. | 0.24 | — | — |
| 4 | C | 17 | 102 | 60 | 50 mL | 150 min. | 60 min. | 0.23 | 96% | — |
| 5 | D | 14.6 | 88 | 65 | 50 mL | 10 min. | 180 min. | 0.20 | — | — |
| 6 | D | 15 | 90 | 100 | 100 mL | 10 min. | 300 min. | 0.148 | ~100% | 99% |
| 7 | E | 12 | 72 | 100 | 100 mL | 10 min. | 300 min. | 0.114 | ~100% | 95% |

The tertiaryaminoalkyllithium solutions of examples 1–5 were used to initiate polymerization reactions of butadiene and styrene-butadiene blends. The general procedure for these polymerizations is as follows: To a solution of monomer in a dry, nitrogen purged bottle capped with a Viton septum was added the desired amount of initiator solution via syringe. To the resulting solution was then added a polar modifier and the mixture was then agitated at 50° C. for 1.5 to 18 hours before being quenched with 1.5 mL of i-ProH and treated with antioxidant (3.5 mL of 1.6 wt. % di-t-butyl paracresol solution in hexane). Polymers were then drum dried directly from the cement. Data from the polymerizations are given in Table II. Polymer data are given in Table III.

TABLE II

| Example | Initiator from Example | Desired Mn | Monomer (g) | mmoles Init. | mL Init. | mL OOOPs | Polymerization Time (h) |
|---|---|---|---|---|---|---|---|
| 8 | 1 | 150000 | *BD(77.7) | 0.518 | 2.16 | 0.06 | 1.5 |
| 9 | 1 | 150000 | BD(75.0) | 0.5 | 2.08 | 0.05 | 1.5 |
| 10 | 1 | 150000 | BD(80.3) | 0.535 | 2.23 | 0.06 | 1.5 |
| 11 | 2 | 120000 | BD(82.3) | 0.686 | 2.85 | 0.07 | 4 |
| 12 | 2 | 120000 | BD(82.7) | 0.689 | 2.87 | 0.07 | 4 |
| 13 | 2 | 100000 | BD(84.8) | 0.847 | 3.52 | 0.08 | 4 |
| 14 | 2 | 150000 | BD(81.2) | 0.541 | 2.25 | 0.06 | 4 |
| 15 | 3 | 100000 | *S/BD(73.2) | 0.732 | 3.48 | 0.07 | 18 |
| 16 | 3 | 120000 | S/BD(67.1) | 0.56 | 2.66 | 0.06 | 18 |

TABLE II-continued

| Example | Initiator from Example | Desired Mn | Monomer (g) | mmoles Init. | mL Init. | mL OOOPs | Polymerization Time (h) |
|---|---|---|---|---|---|---|---|
| 17 | 3 | 120000 | S/BD(71.5) | 0.596 | 2.84 | 0.06 | 18 |
| 18 | 3 | 150000 | S/BD(68.5) | 0.457 | 2.17 | 0.O5 | 18 |
| 19 | 4 | 100000 | BD(58.5) | 0.584 | 2.43 | 0.06 | 18 |
| 20 | 4 | 120000 | BD(63.5) | 0.423 | 1.76 | 0.04 | 18 |
| 21 | 4 | 130000 | BD(59.7) | 0.459 | 1.91 | 0.05 | 18 |
| 22 | 4 | 150000 | BD(57.0) | 0.38 | 1.58 | 0.04 | 18 |
| 23 | 5 | 100000 | S/BD(64.1) | 0.641 | 3.28 | 0.06 | 18 |
| 24 | 5 | 120000 | S/BD(62.6) | 0.521 | 2.67 | 0.O5 | 18 |
| 25 | 5 | 120000 | S/BD(68.2) | 0.568 | 2.91 | 0.06 | 18 |
| 26 | 5 | 150000 | S/BD(63.4) | 0.423 | 2.16 | 0.04 | 18 |

*BD is butadiene and S is styrene.

TABLE III

| Example | Initiator from Example | Mn | Mw/Mn | % 1,2-Vinyl |
|---|---|---|---|---|
| 8 | 1 | 157,000 | 1.07 | 35.7 |
| 9 | 1 | 170,000 | 1.08 | 41.3 |
| 10 | 1 | 155,000 | 1.1 | 38.3 |
| 11 | 2 | 125,000 | 1.06 | 29 |
| 12 | 2 | 117,000 | 1.07 | 29.4 |
| 13 | 2 | 98,000 | 1.07 | 28.9 |
| 14 | 2 | 150,000 | 1.08 | 27.2 |
| 15 | 3 | 98,000 | 1.08 | 30.6 |
| 16 | 3 | 118,000 | 1.07 | 31.2 |
| 17 | 3 | 112,000 | 1.09 | 28.7 |
| 18 | 3 | 148,000 | 1.1 | 29.0 |
| 19 | 4 | 96,090 | 1.15 | 34 |
| 20 | 4 | 127,000 | 1.13 | 28 |
| 21 | 4 | 114,000 | 1.1 | 31.3 |
| 22 | 4 | 138,000 | 1.1 | 30.9 |
| 23 | 5 | 109,000 | 1.23 | 31.4 |
| 24 | 5 | 136,000 | 1.19 | 30 |
| 25 | 5 | 136,000 | 1.19 | 31.8 |
| 26 | 5 | 184,000 | 1.15 | 29.1 |

As apparent from the above Tables, high yield, and high purity initiators were obtained which resulted in the production of high molecular weight rubbers generally having low Mw/Mn ratios. Example 5 was tested by gas chromatography for stability, and at room temperature (20° C.) had a decay of less than 2 mole percent after 8 weeks.

While in accordance with the patent statutes the best mode and preferred embodiment has been set forth, the scope of the invention is not limited thereto, but rather by the scope of the attached claims.

What is claimed is:

1. An initiator solution, comprising;

a moderate temperature stable anionic initiator composition contained in a hydrocarbon solution, said moderate temperature being from about −20° C. to about 60° C., said anionic initiator being an aminoalkyllithium initiator of the formula

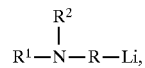

Formula I

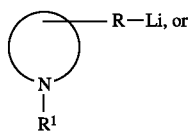

Formula II

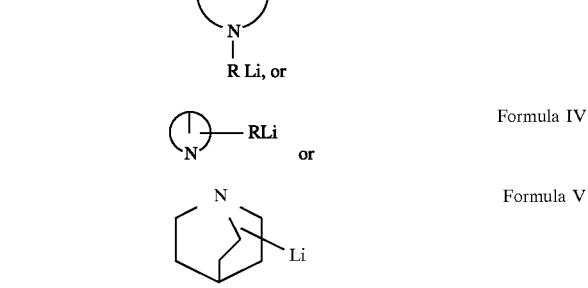

wherein $R^1$ and $R^{22}$, independently, are an alkyl having from 1 to 12 carbon atoms, wherein R is an alkylene or cycloalkylene having 1 to 10 carbon atoms, and optionally including from 1 to 4 alkyl substituents on each ring wherein said alkyl contains from 1 to 4 carbon atoms, wherein the amount of said anionic initiator in said composition is at least a 60 percent yield based upon a starting material which is a halide of said Formulas I, II, III, IV, or V, or combinations thereof.

2. An initiator solution according to claim 1, wherein said aminoalkyllithium initiator has a stability of less than 1 mole percent decay per week at 20° C., and wherein said anionic initiator composition has a purity of at least 60 percent by weight.

3. An initiator solution according to claim 2, wherein said purity of said aminoalkyllithium initiator composition is at least 90 percent by weight, and wherein said yield is at least 90 percent.

4. An initiator solution according to claim 3, wherein the purity of said aminoalkyllithium initiator composition is at least 95 percent by weight, wherein said yield is at least 95 percent, wherein said moderate temperature is from about 10° C. to about 30° C., and wherein said hydrocarbon solvent is an alkane, a cycloalkane, or an aromatic having from 5 or 6 to about 30 carbon atoms.

5. An initiator solution according to claim 4, wherein said aminioalkyllithium initiator has a stability of less than 0.3 mole percent decay per week at 20° C., and wherein said aminoalkyl lithium initiator is 3-hexamethyleneiminepropyl lithium, 3-dimethylaminopropyl lithium, 2-(2-lithiummethyl)-1-methylpyrrolidine, 3-lithiummethyl-1-methylpiperidine, or 3-pyrrolidinopropyl lithium, or combinations thereof.

6. A process for producing an anionic initiator solution, comprising the steps of:

reacting an aminoalkylhalide compound of the formula

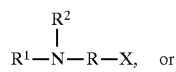  Formula I

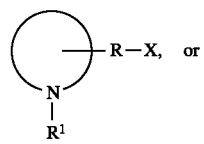  Formula II

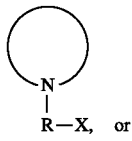  Formula III

  Formula IV

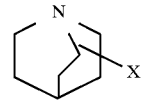  Formula V wherein $R^1$ and $R^2$, independently, are an alkyl having from 1 to 12 carbon atoms, wherein R is an alkylene or cycloalkylene having from 1 to 10 carbon atoms, wherein X is a halide, and optionally including from 1 to 4 alkyl substituents on each ring wherein said alkyl substituent contains from 1 to 4 carbon atoms, with an excess of lithium in the presence of an organic ether at or below the temperature of the boiling point of said organic ether to form an anionic initiator, said organic ether having the formula $R^3\text{-O-}R^4$ where $R^3$ and $R^4$, independently, are an alkyl having from 1 to 4 carbon atoms, and removing said organic ether and adding a hydrocarbon solvent to form an ambient temperature stable initiator.

7. A process according to claim 6, wherein $R^3$ is methyl and $R^4$ is methyl or ethyl, and wherein the mole ratio of said lithium to said aminoalkylhalide is from about 2 to about 12.

8. A process according to claim 7, wherein said hydrocarbon solvent is an alkane, a cycloalkane, or an aromatic, or combinations thereof, having from 5 or 6 carbon atoms to about 30 carbon atoms and, wherein said anionic initiator has a stability of less than 1.0 mole percent decay per week at 20° C.

9. A process according to claim 8, wherein said mole ratio is from about 2 to about 4, wherein said reaction temperature is from about minus 25° C. to about minus 78° C., and wherein said ether is dimethyl ether.

10. A process according to claim 9, wherein said anionic initiator has a stability of less than 0.3 mole percent decay per week at 20° C., and wherein said aminoalkylhalide is 3-hexamethyleneiminepropyl chloride, 3-dimethylaminopropyl chloride, 2-(2-chloroethyl)-1-methylpyrrolidine, 3-chloromethyl-1-methylpiperidine, or 3-pyrrolidinopropyl chloride, or combinations thereof.

11. An anionic initiator solution made by reacting a tertiaryaminoalkylhalide with an excess of lithium in the presence of an organic ether at or below the boiling point of said ether and replacing said ether with a hydrocarbon solvent, said organic ether having the formula $R^3\text{-O-}R^4$ where $R^3$ and $R^4$, independently, are an alkyl having from 1 to 4 carbon atoms, wherein said initiator is stable in said hydrocarbon solvent at a moderate temperature, wherein the stability of said anionic initiator is less than 1 percent mole decay per week at 20° C., and wherein the purity of said anionic initiator solution is at least 80 percent by weight.

12. An anionic initiator solution according to claim 11, wherein the mole ratio of said lithium to said tertiaryaminoalkylhalide is from about 2 to about 9, wherein $R^3$ is methyl and $R^4$ is methyl or ethyl, and wherein said moderate temperature is from about minus 20° C. to about 60° C.

13. An anionic initiator solution according to claim 12, wherein said purity is at least 90 percent by weight, and wherein said reaction is at a temperature of from about minus 25° C. to about minus 78° C.

14. An anionic initiator solution according to claim 13, wherein said tertiaryaminoalkylhalide is

  Formula I

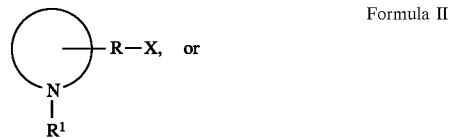  Formula II

  Formula III

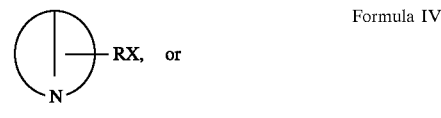  Formula IV

  Formula V wherein $R^1$ and $R^2$, independently, are an alkyl having from 1 to 12 carbon atoms, wherein R is an alkylene or cycloalkylene having 1 to 10 carbon atoms, and wherein X is a halide, and optionally including from 1 to 4 alkyl substituents on each ring wherein said alkyl substituent contains from 1 to 4 carbon atoms, wherein said stability is less than 0.5 mole percent decay per week, wherein said mole ratio is from about 2 to about 4, and wherein said ether is dimethylether.

15. An anionic initiator solution according to claim 14, wherein said hydrocarbon solvent is an alkane, cycloalkane, aromatic, or combinations thereof, having from 5 or 6 carbon atoms to about 30 carbon atoms, and wherein said tertiaryaminoalkylhalide is 3-hexamethyleneiminepropyl chloride, 3-dimethylaminopropyl chloride, 2-(2-chloroethyl)-1-methylpyrrolidine, 3-chloromethyl-1-methylpiperidine, or 3-pyrrolidinopropyl chloride, or combinations thereof.

* * * * *